(12) United States Patent
Kahn et al.

(10) Patent No.: US 6,417,412 B1
(45) Date of Patent: Jul. 9, 2002

(54) PURIFICATION OF TERTIARY BUTYL ALCOHOL

(75) Inventors: Andrew P. Kahn, Eagleville; Lawrence J. Karas, West Chester, both of PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 10/005,110

(22) Filed: Dec. 3, 2001

(51) Int. Cl.⁷ .................................................. C07C 21/34
(52) U.S. Cl. ....................................... 568/917; 568/913
(58) Field of Search ................................... 568/913, 917

(56) References Cited

U.S. PATENT DOCUMENTS

| | | | |
|---|---|---|---|
| 4,239,926 A | | 12/1980 | Grane et al. |
| 4,543,432 A | * | 9/1985 | Shih et al. |
| 6,037,516 A | | 3/2000 | Morford et al. |
| 6,069,287 A | | 5/2000 | Ladwig et al. |
| 6,133,484 A | | 10/2000 | Knifton et al. |

* cited by examiner

*Primary Examiner*—Alan Siegel
(74) *Attorney, Agent, or Firm*—William C. Long

(57) ABSTRACT

The present invention relates to purification of a tertiary butyl alcohol process stream by contact in the liquid phase with a large pore zeolite such as 13X in the sodium form.

3 Claims, No Drawings

PURIFICATION OF TERTIARY BUTYL ALCOHOL

BACKGROUND OF THE INVENTION

1. Field of the Invention

The present invention relates to the purification of tertiary butyl alcohol and especially to the separation of minor amounts of close boiling oxygenated impurities therefrom by contacting the impure tertiary butyl alcohol with a large pore zeolite such as 13X zeolite in the sodium form.

2. Description of the Prior Art

Generally tertiary butyl alcohol as produced by oxidation processes such as the Oxirane Process contains small but significant amounts of impurities including water, isopropanol, acetone, methyl ethyl ketone, isobutanal formate esters, secondary butyl alcohol and the like. In certain applications the presence of such impurities causes problems with respect to the desired use. It is desirable to provide a process by which the impurities can be conveniently separated.

It is known that the close boiling oxygenated impurities can be separated to a significant degree from tertiary butyl alcohol by an elaborate and extensive distillation procedure. See U.S. Pat. No. 4,239,926. However, such procedures are costly and time consuming, involving as they do substantial capitol investments and utilities expenses.

U.S. Pat. No. 4,543,432 shows the separation of isopropanol form a tertiary butyl alcohol process stream by absorption in an asymmetric carbonacems absorbent such as Ambersorb® XE-347. Data are presented in Table II giving the equilibrium capacity of isopropanol on various adsorbents for a synthic solution of isopropanol in tertiary butanol. Data for Type JA and 13X molecular sieves are given indicating that Type JA has a slightly higher equilibrium capacity than Type 13X. Additional data relative to Type JA are given in Table IV.

It is desirable to have a simplified procedure whereby tertiary butyl alcohol process streams can be conveniently treated to separate close boiling impurities by a relatively simple and straight forward procedure.

SUMMARY OF THE INVENTION

In accordance with the present invention, a tertiary butyl alcohol process stream containing minor amounts of the impurities which are normally associated with the tertiary butyl alcohol, is contacted in the liquid phase with a large pore zeolite such as 13X zeolite or zeolite Y in the sodium form. As a result of this contact, impurities are retained on the zeolite and are thus removed or separated from the tertiary butyl alcohol; product tertiary butyl alcohol reduced in the content of contaminating impurities is readily recovered. It is generally advantageous to operate with a plurality of contact zones since the contact material must be regenerated from time to time as it loses its effectiveness for impurities removal over extended use. With a plurality of treatment zones, tertiary butyl alcohol can be treated in one zone while a separate zone is being regenerated.

DETAILED DESCRIPTION

Tertiary butyl alcohol as produced commercially, for example by the Oxirane Process, contains small but significant amounts of impurities, e.g. 0.1 to about 2.0 wt %. Illustrative of such impurities are water, isopropanol, acetone, methyl ethyl ketone, isobutanol, formate esters, and secondary butyl alcohol. The tertiary butyl alcohol stream to be treated illustratively comprises by weight about 10 ppm to 2% of each of the above impurities, usually about 20 ppm to 1% of each. Other materials which can readily be separated as by distillation such as methanol and methyl tertiary butyl ether may also be present. In accordance with the present invention, the impure tertiary butyl alcohol in the liquid phase is contacted with solid sodium form large pore zeolite such as 13X zeolite whereby impurities are retained on the contact zeolite solid and a liquid product tertiary butyl alcohol reduced in impurities content is conveniently separated. The contact takes place at moderate temperatures, illustratively 0 to 150° C., although temperature is not critical. The contact solid retains the impurities adsorbed thereon and purified tertiary butyl alcohol can be separated. Initially, there can be substantially complete removal of the impurities and the recovered tertiary butyl alcohol is of exceptional purity. Over the course of time the contact solid gradually becomes less effective for the removal of these components. In accordance with the present invention at a pre-determined time when the separation efficiency has fallen below a desired point, the solid contact material is effectively regenerated, as by contact with a heated vapor stream such as nitrogen or air at a temperature of at least 3000 or by wash with a solvent such as methanol or water. It is advantageous to employ a plurality of parallel contact zones such that while one zone is being regenerated the feed is passed through a zone containing fresh or regenerated contact material so that optimum impurities removal can be achieved.

The zeolitic contact materials used in the present invention are those of large pore diameter (10 Angstroms) illustrated by 13X or zeolite Y.

The large pore zeolites are useful for the removal of essentially all of the impurities as above described, which are normally associated with tertiary butyl alcohol process streams.

A critical feature of the present invention is that the large pore zeolite be in the sodium form rather than the acid form in order to provide effective impurities removal.

In order to illustrate practice of the invention the following examples are provided.

EXAMPLE 1

A 1.0 cm ID jacketed column was charged with 91 cc of Zeolite Y in the sodium form ($SiO_2/Al_2O_3$=5.1) that had been ground to 14/30 mesh and heated for 18 hours at 300° C. in nitrogen. A feed comprised of 93.98 wt % TBA, 4.04 wt % isooctane, 0.61 wt % water, 0.48 wt % acetone, 0.24 wt % IPA, 0.10 wt % SBA, 0.32 wt % TBF, 0.08 wt % iBuOH, and 0.13 wt % IBF was pumped across the bed at 95 cc/min. Samples were taken in 25 cc cuts for analysis. The results are presented in Table 1:

TABLE 1

| Cut # | 1 | 4 |
| --- | --- | --- |
| % Acetone Removed | 100 | 100 |
| % IPA Removed | 100 | 100 |
| % MEK Removed | 100 | 100 |
| % SBA Removed | 100 | 100 |
| % TBF Removed | 100 | 100 |
| % iBuOH Removed | 91.9 | 80.9 |
| % IBF Removed | 100 | 100 |
| Wt % Water in Sample | 0.046 | 0.021 |

It can be seen that Zeolite Y in the sodium form is highly effective for removing impurities from tertiary butyl alcohol.

By way of contrast, the following comparative Examples 1–3 demonstrate that Zeolite Y in the acid form is very much less effective.

COMPARATIVE EXAMPLE 1

Example 1 was repeated using 85 cc of Zeolite Y in the acid form ($SiO_2/Al_2O_3=5.2$) and a feed rate of 82 cc/min. The results are presented in Table 2:

TABLE 2

| Cut # | 1 | 4 |
|---|---|---|
| % Acetone Removed | 100 | 0 |
| % IPA Removed | 58.8 | 0 |
| % MEK Removed | 100 | 0 |
| % SBA Removed | 42.0 | 0 |
| % TBF Removed | 84.8 | 2.1 |
| % iBuOH Removed | 0 | 0 |
| % IBF Removed | 82.5 | 0 |
| Wt % Water in Sample | 0.061 | 0.14 |

COMPARATIVE EXAMPLE 2

Example 1 was repeated using 86 cc of Zeolite Y in the acid form ($SiO_2/Al_2O_3=60$) and a feed rate of 92 cc/min. The results are presented in Table 3:

TABLE 3

| Cut # | 1 | 4 |
|---|---|---|
| % Acetone Removed | 97.0 | 0 |
| % IPA Removed | 34.7 | 0.8 |
| % MEK Removed | 90.6 | 0 |
| % SBA Removed | 24.0 | 0.3 |
| % TBF Removed | 8.0 | 0 |
| % iBuOH Removed | 0 | 0 |
| % IBF Removed | 27.0 | 0 |
| Wt % Water in Sample | 0.95 | 0.82 |

COMPARATIVE EXAMPLE 3

Example 1 was repeated using 86 cc of Zeolite Y in the acid form ($SiO_2/Al_2O_3=80$) and a feed rate of 89 cc/min. The results are presented in Table 4:

TABLE 4

| Cut # | 1 | 4 |
|---|---|---|
| % Acetone Removed | 58.5 | 0 |
| % IPA Removed | 1.2 | 0.6 |
| % MEK Removed | 26.6 | 0 |
| % SBA Removed | 0 | 0 |
| % TBF Removed | 0 | 0 |
| % iBuOH Removed | 0 | 0 |
| % IBF Removed | 4.2 | 0 |
| Wt % Water in Sample | 1.57 | 0.78 |

Comparative Example 1–3 show the necessity of having the sodium form of Y-zeolite with a low $SiO_2/Al_2O_3$ ratio.

EXAMPLE 2

Example 1 was repeated using 93 cc of 13X molecular sieve and a feed comprised of 97.51% TBA, 0.61 wt % water, 0.79 wt % acetone, 0.25 wt % IPA, 0.12 wt % MEK, 0.04 wt % SBA, 0.39 wt % TBF, 0.10 wt % iBuOH, and 0.20 wt % IBF. The column was heated to 40° C. and the feed was pumped across the bed at 88 cc/min. Samples were collected in 50 cc cuts for analysis. The results are presented in Table 5:

TABLE 5

| Cut # | 1 | 2 |
|---|---|---|
| % Acetone Removed | 100 | 100 |
| % IPA Removed | 100 | 100 |
| % MEK Removed | 100 | 100 |
| % SBA Removed | 100 | 100 |
| % TBF Removed | 97.0 | 69.2 |
| % iBuOH Removed | 100 | 100 |
| % IBF Removed | 100 | 100 |
| Wt % Water in Sample | 0.044 | 0.044 |

Contact was continued until impurities breakthrough was observed at which the 1 3X was regenerated by contact with nitrogen at about 300° C.

After 10 such cycles, the capacity of the 13X for impurities removal was essentially unchanged.

Example 2 demonstrates that 13X molecular sieve (which is in the sodium form) is also highly effective for impurities removal.

COMPARATIVE EXAMPLE 4

Example 1 was repeated using 89 cc of 5A molecular sieve and a feed comprised of 92.91% TBA, 4.73 wt % isooctane, 0.61 wt % water, 0.73 wt % acetone, 0.23 wt % IPA, 0.11 wt % MEK, 0.04 wt % SBA, 0.36 wt % TBF, 0.09 wt % iBuOH, and 0.18 wt % IBF. The feed was pumped across the bed at 92 cc/min. Samples were collected in 25 cc cuts for analysis. The results are presented in Table 6.

TABLE 6

| Cut # | 1 | 4 |
|---|---|---|
| % Acetone Removed | 48.9 | 19.8 |
| % IPA Removed | 6.1 | 2.1 |
| % MEK Removed | 17.6 | 3.8 |
| % SBA Removed | 0 | 0 |
| % TBF Removed | 6.7 | 0.6 |
| % iBuOH Removed | 20 | 0 |
| % IBF Removed | 4.3 | 0.1 |
| Wt % Water in Sample | 0.012 | 0.093 |

This Comparative Example demonstrates that 5A molecular sieve is ineffective for impurities removal.

COMPARATIVE EXAMPLE 5

Example 1 was repeated using 86 cc of zeolite ZSM-5 ($SiO_2/Al_2O_3=80$) and a feed rate of 76 cc/min. The results are presented in Table 7:

TABLE 7

| Cut # | 1 | 4 |
|---|---|---|
| % Acetone Removed | 100 | 100 |
| % IPA Removed | 100 | 100 |
| % MEK Removed | 100 | 100 |
| % SBA Removed | 100 | 100 |
| % TBF Removed | 31.3 | 8.9 |
| % iBuOH Removed | 91.1 | 28.7 |
| % IBF Removed | 100 | 100 |
| Wt % Water in Sample | 3.60 | 1.30 |

This example demonstrates the inefficiency of removing TBF and iBuOH as well as significant dehydration of TBA to produce water and isobutylene with ZSM-5.

COMPARATIVE EXAMPLE 6

Comparative Example 5 was repeated using 85 cc of zeolite ZSM-5 ($SiO_2/Al_2O_3=80$) that had been steamed to reduce acidity and a feed rate of 90 cc/min. The results are presented in Table 8:

TABLE 8

| Cut # | 1 | 4 |
|---|---|---|
| % Acetone Removed | 100 | 100 |
| % IPA Removed | 100 | 100 |
| % MEK Removed | 100 | 100 |
| % SBA Removed | 100 | 100 |
| % TBF Removed | 58.4 | 13.6 |
| % iBuOH Removed | 73.6 | 0 |
| % IBF Removed | 100 | 100 |
| Wt % Water in Sample | 1.80 | 1.00 |

This example show that steaming the zeolite to reduce acidity, reduces the dehydration but still does not give acceptable removal or TBF of iBuOH.

COMPARATIVE EXAMPLE 7

Comparative Example 5 was repeated using 97 cc of zeolite ZSM-5 ($SiO_2/Al_2O_3=80$) that had been ion exchanged with sodium acetate (finished zeolite contained 0.52 wt % Na) and a feed rate of 99 cc/min. The results are presented in Table 9:

TABLE 9

| Cut # | 1 | 4 |
|---|---|---|
| % Acetone Removed | 100 | 100 |
| % IPA Removed | 100 | 100 |
| % MEK Removed | 100 | 100 |
| % SBA Removed | 100 | 100 |
| % TBF Removed | 58.6 | 24.3 |
| % iBuOH Removed | 86.4 | 19.3 |

TABLE 9-continued

| Cut # | 1 | 4 |
|---|---|---|
| % IBF Removed | 100 | 100 |
| Wt % Water in Sample | 5.6 | 1.30 |

This example shows that sodium treating the ZSM resulted in increased dehydration with some improvement in removing TBF and iBuOH.

In the above Examples, the following abbreviations are used:

TBA=tertiary butyl alcohol

IPA=isopropanol

MEK=methyl ethyl ketone

SBA=secondary butyl alcohol

TBF=tertiary butyl formate

IBuOH=isobutanol

IBF=isobutyl formate.

We claim:

1. The method of separating impurities from a tertiary butyl alcohol process stream feed containing a minor quantity of said impurities which comprises passing the tertiary butyl alcohol feed in the liquid phase into contact with a solid large pore zeolite selected from the group consisting of Zeolite 13X and Zeolite Y in the sodium form and recovering a tertiary butyl alcohol product stream reduced in content of said impurities.

2. The method of claim 1 wherein the zeolite is 13X.

3. The method of claim 1 wherein the zeolite is zeolite Y.

* * * * *